US012586672B2

(12) United States Patent
Hyvönen et al.

(10) Patent No.: US 12,586,672 B2
(45) Date of Patent: Mar. 24, 2026

(54) INTELLIGENT TREATABLE SECTORS FOR RADIATION THERAPY PLAN GENERATION

(71) Applicant: Siemens Healthineers International AG, Steinhausen (CH)

(72) Inventors: Heini Hyvönen, Helsinki (FI); Mikko Hakala, Rajamäki (FI); Ville Pietilä, Helsinki (FI); Hannu Laaksonen, Espoo (FI)

(73) Assignee: Siemens Healthineers International AG, Steinhausen (CH)

( * ) Notice: Subject to any disclaimer, the term of this patent is extended or adjusted under 35 U.S.C. 154(b) by 261 days.

(21) Appl. No.: 18/129,403

(22) Filed: Mar. 31, 2023

(65) Prior Publication Data

US 2024/0331833 A1      Oct. 3, 2024

(51) Int. Cl.
*A61N 5/10*      (2006.01)
*G16H 20/40*      (2018.01)
(52) U.S. Cl.
CPC ............. *G16H 20/40* (2018.01); *A61N 5/103* (2013.01)
(58) Field of Classification Search
CPC ............................... A61N 5/103; G16H 20/40
See application file for complete search history.

(56) References Cited

U.S. PATENT DOCUMENTS

2019/0051398 A1      2/2019      Zankowski et al.
2021/0339048 A1      11/2021      Nguyen et al.

2021/0387018 A1      12/2021      Hakala et al.
2022/0088410 A1      3/2022      Hibbard
2022/0093242 A1      3/2022      Hakala et al.
2022/0414525 A1      12/2022      Princ et al.

FOREIGN PATENT DOCUMENTS

WO      WO-2017152286 A1 *      9/2017      ............. A61N 5/103
WO      WO-2022/271197 A1      12/2022

OTHER PUBLICATIONS

Amit Guy et al: "Automatic learning-based beam angle selection for thoracic IMRT", Medical Physics, AIP, Melville, NY, US, vol. 42, No. 4, Apr. 30, 2015 (Apr. 30, 2015),—Apr. 30, 2015 (Apr. 30, 2015), pp. 1992-2005, XP012195734, ISSN: 0094-2405, DOJ:: 10.1118/1.4908000 [retrieved on Jan. 1, 1901] the whole document.
International Search Report and Written Opinion dated May 15, 2024 on PCT App. PCT/EP2024/057665 (16 pages).
International Standard, "Radiotherapy equipment—Coordinates movements and scales" IEC 61217, Edition 2.0, Dec. 2011.

* cited by examiner

*Primary Examiner* — Mark R Gaworecki
(74) *Attorney, Agent, or Firm* — Foley & Lardner LLP

(57)      ABSTRACT

Disclosed herein are methods and systems for calculating radiation therapy treatment plan (RTTP) including a method that comprises monitoring, by a processor, a treatment plan optimizer computer model to identify a set of treatment plans, where the treatment plan optimizer computer model ingests a set of medical images and predicts each treatment plan comprising a respective range of angles for treatment beam entry; generating, by the processor, a training dataset comprising the monitored data; and training, by the processor, a machine learning model using the training dataset to predict a new range of angles for treatment beam entry for a new patient by ingesting new patient data of the new patient.

20 Claims, 17 Drawing Sheets

200

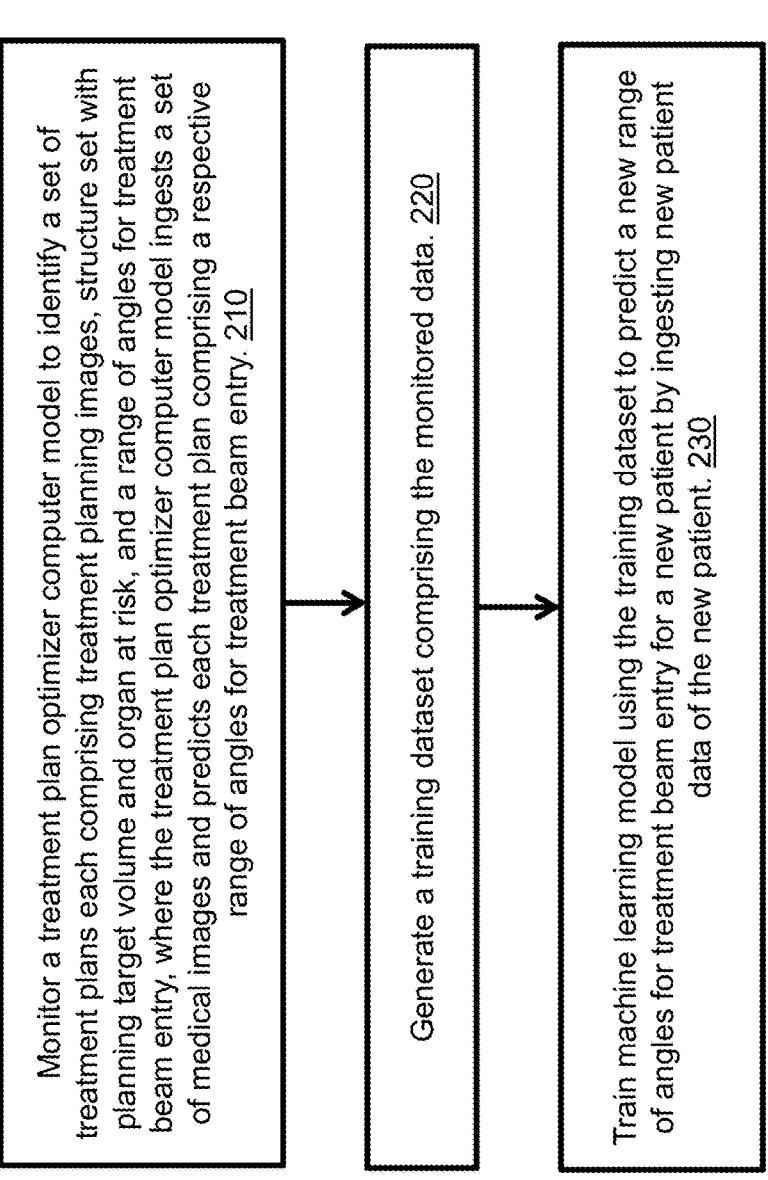

Monitor a treatment plan optimizer computer model to identify a set of treatment plans each comprising treatment planning images, structure set with planning target volume and organ at risk, and a range of angles for treatment beam entry, where the treatment plan optimizer computer model ingests a set of medical images and predicts each treatment plan comprising a respective range of angles for treatment beam entry. 210

Generate a training dataset comprising the monitored data. 220

Train machine learning model using the training dataset to predict a new range of angles for treatment beam entry for a new patient by ingesting new patient data of the new patient. 230

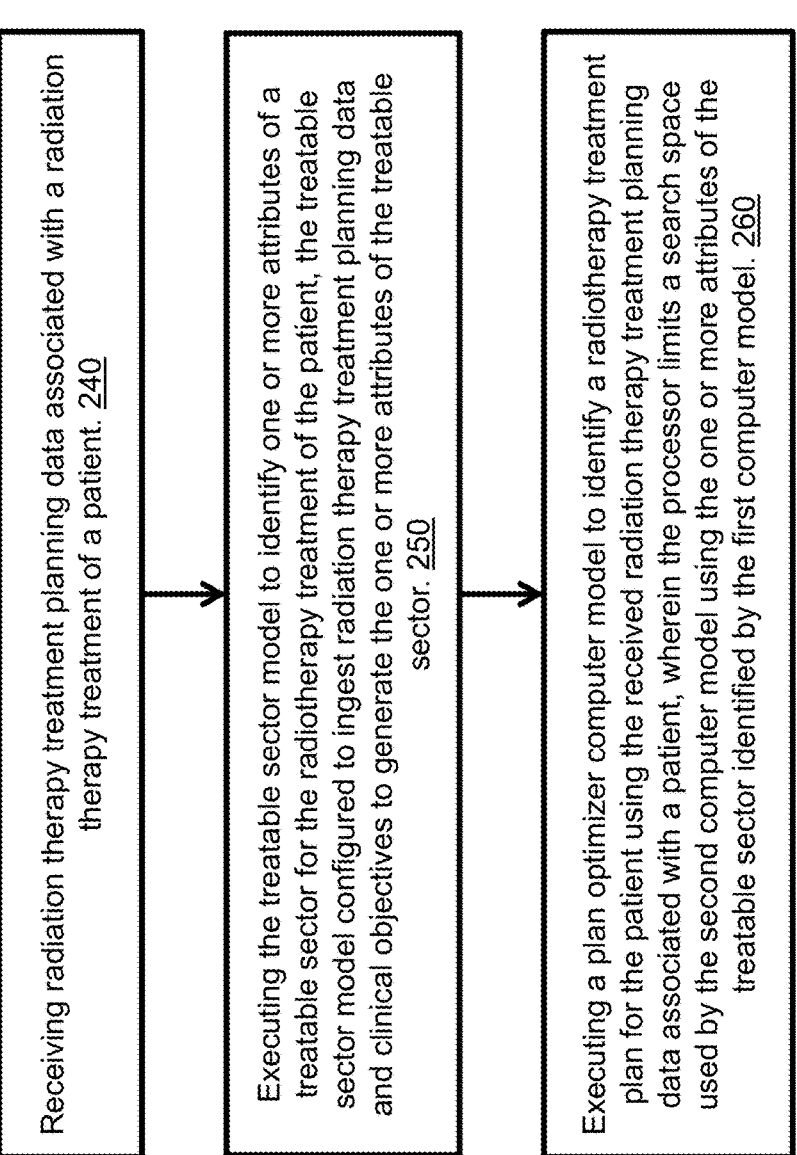

Receiving radiation therapy treatment planning data associated with a radiation therapy treatment of a patient. 240

Executing the treatable sector model to identify one or more attributes of a treatable sector for the radiotherapy treatment of the patient, the treatable sector model configured to ingest radiation therapy treatment planning data and clinical objectives to generate the one or more attributes of the treatable sector. 250

Executing a plan optimizer computer model to identify a radiotherapy treatment plan for the patient using the received radiation therapy treatment planning data associated with a patient, wherein the processor limits a search space used by the second computer model using the one or more attributes of the treatable sector identified by the first computer model. 260

Lung 316a

Lung 316b

L

Treatable Sector 312

R

PTV 314

320

Lung 326a

Lung 326b

L

Treatable Sector 322

R

PTV 324

330

Treatable Sector 332

L

PTV 334

R

Lung 336a

Lung 336b

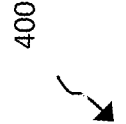
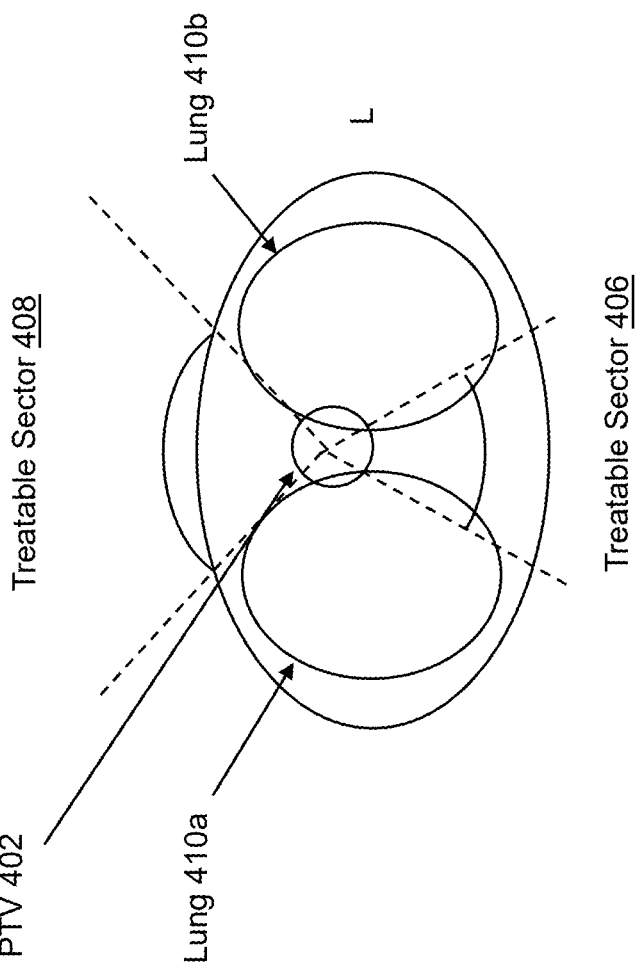
FIG. 4

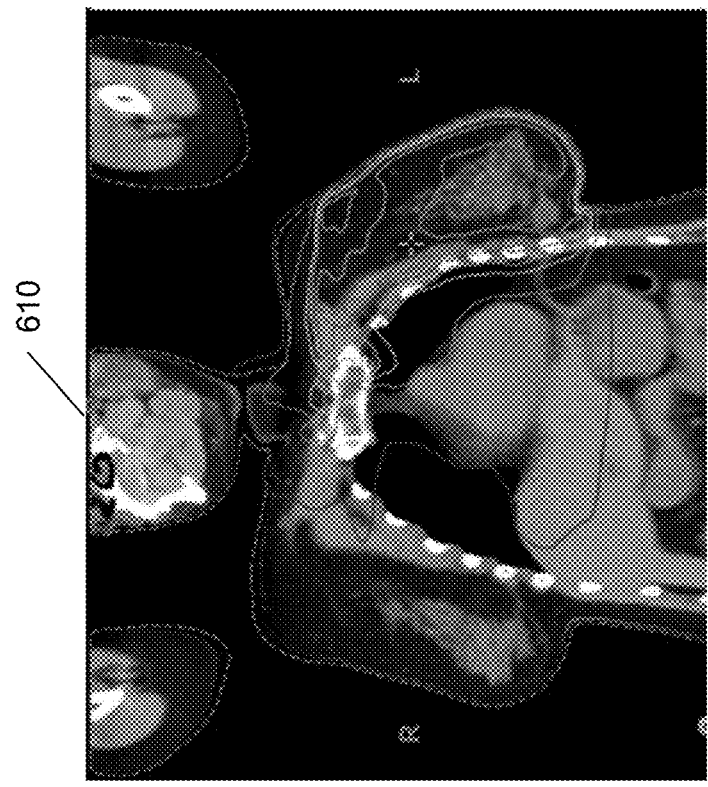
610
600
FIG. 6 https://commons.wikimedia.org/wiki/File:VGG16.png

| name | arc | arc_true |
|---|---|---|
| Extended left | | |
| Breast03_rome | [299.2 165.7] | [302, 170] |
| Breastnorsk_00003 | [298.9 166.9] | [305, 170] |
| Breastnorsk_00010 | [300.7 164.5] | [305, 179] |
| Estro2015Breast | [297.3 167.6] | [307, 170] |
| Extended right | | |
| Breastnorsk_00017 | [189.5 49.7] | [190, 51] |
| Breastnorsk_00019 | [189.6 49.9] | [190, 46] |
| BRe_06 | [189.1 52.5] | [190, 54] |
| BRe_07 | [188.6 50.6] | [190, 50] |
| Left | | |
| 62 | [298.1 160.3] | [300, 160] |
| 152 | [296.5 158.4] | [300, 160] |
| 153 | [297.9 166.3] | [310, 160] |
| 154 | [296.8 158.2] | [320, 160] |
| Breast_Hypo_SIB_10 | [300.6 156.4] | [290, 160] |
| Right | | |
| 73 | [201.1 57.5] | [200, 50] |
| 74 | [201.6 54.5] | [200, 60] |
| 157 | [207.9 55.7] | [210, 60] |
| 159 | [208.2 57.3] | [210, 60] |

810

| Case | Average Predicted posterior angle | True average |
|---|---|---|
| Extended left | 166 | 170 |
| Extended right | 189 | 190 |
| Left | 160 | 160 |
| Right | 205 | 205 |

| Method | Sampling (deg) | Average error |
|---|---|---|
| Start/Stop angle | 3 | 4.1 |
| Start/Stop angle | 4 | 5.1 |
| Propability distribution | 4 | 4.1 |

| Case | Start | Stop |
|---|---|---|
| 1 | 303.3 | 159.6 |
| 2 | 304.8 | 159.4 |
| 3 | 300.8 | 154.6 |
| 4 | 296.6 | 168.6 |
| 5 | 301.6 | 159.7 |
| 6 | 190.8 | 50.5 |
| 7 | 197.6 | 59.4 |

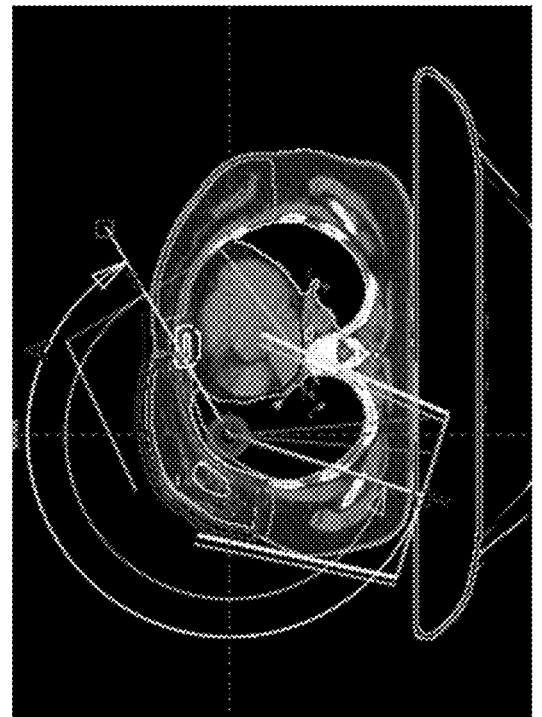
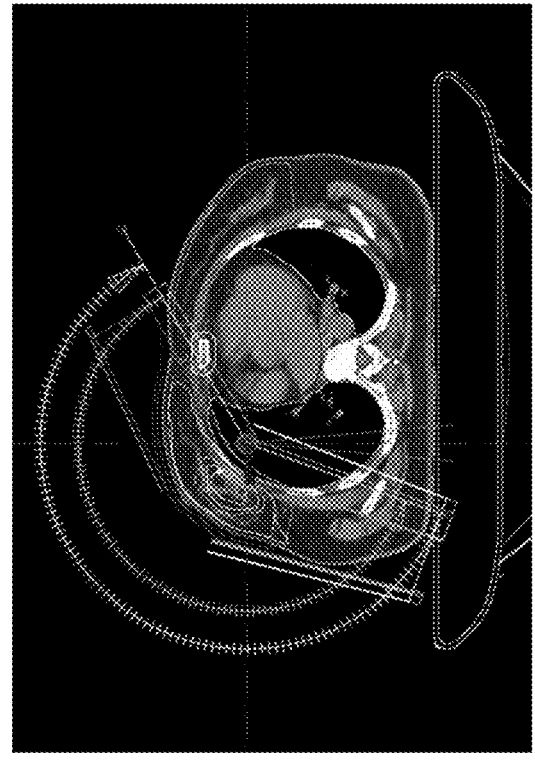
FIG. 15

FIG. 16

INTELLIGENT TREATABLE SECTORS FOR RADIATION THERAPY PLAN GENERATION

TECHNICAL FIELD

This application relates generally to using computer modeling techniques, such as machine learning techniques, to generate radiation therapy treatment plans and to control radiation therapy machines.

BACKGROUND

Radiation therapy (radiation-based therapy or radiotherapy) is used as a cancer treatment to emit high doses of radiation that can kill cells or shrink a tumor. The target region of a patient's body that is intended to receive radiation (e.g., tumor) is referred to as the planning target volume (PTV). The goal is to deliver enough radiation to the PTV to kill the cancerous cells during a radiation therapy treatment (also referred to herein as a treatment plan or radiation therapy treatment). However, other organs or anatomical regions that are adjacent to or surround the PTV can be in the path of radiation beams and can receive enough radiation to damage or harm such organs or anatomical regions. These organs or anatomical regions are referred to as organs at risk (OARs). Usually, a physician or a radiologist identifies both the PTV and the OARs before radiation therapy using, for example, computed tomography (CT) images, magnetic resonance imaging (MRI) images, positron emission tomography (PET) images, images obtained via some other imaging modality, or a combination thereof.

Using the medical images of the patient as well as the identified PTV and the OARs, a team of medical professionals (e.g., physicians, radiologists, oncologists, radiology technicians, other medical personnel, or a combination thereof) determines the radiation parameters to be used during the radiation therapy treatment. These radiation parameters may include, for example, the type, the angle, the radiation intensity, and/or the shape of each radiation beam. In determining these parameters, the medical professionals attempt to achieve a radiation dose distribution to deliver to the patient that meets predefined criteria (also referred to herein as the plan objectives or clinical objectives). Such criteria usually include predefined radiation dose thresholds or ranges for the PTV and the OARs.

To optimize the radiation parameters in a way to meet the predefined criteria, software solution(s) or a computer model(s) (typically referred to as "plan optimizers") are utilized that can run a plurality of simulations with various radiation parameters and can select a final set of radiation parameters to be used based on the simulation results. These radiation parameters are typically referred to as a radiation therapy treatment plan (RTTP). However, this process can be highly inefficient and undesirable because plan optimizers typically use an iterative, trial-and-error process to optimize various attributes of the RTTP. For instance, after the treating physician inputs the objectives, the software solution iteratively analyzes different possibilities (e.g., different iterations of different attributes within a large search space) to identify one or more beam geometry attributes that yield the best/acceptable results. As a result, the software solutions may require substantial computing resources and may not produce timely results.

Conventional solutions suffer from technical shortcomings because defining beam geometry for treatment planning is especially a complicated process where target size, location, dose prescription, patient condition, and treatment machine limitations (including the risk of collision) all play a role. Designing an automatic algorithm to generate the RTTP is technically challenging because existing solutions provide a mathematical approach that does not consider contextual information regarding the treatment itself. As a result, conventional solutions may place beams/arcs through clinically unacceptable regions simply because the dose distribution satisfies the provided clinical goal limits and minimizes the objective function defined in a mathematical sense. An example of such a situation arises, for example, when a beam enters through the shoulder, nerve roots, or healthy lung. Sometimes, for example, a lung tumor may be centrally located and the beam geometry optimization algorithm may consider both lungs as equally important due to the clinical protocol. Hence, the beam geometry optimization algorithm may place beam/arcs to enter through both lungs. However, the clinical best practice is to avoid placing beam entries through the contra lung. In this example, the beam is mathematically optimized but not medically acceptable. As a result, the algorithm must restart the iteration process to revise the RTTP, which is time-consuming and computationally inefficient.

SUMMARY

For the aforementioned reasons, there is a desire for a system that can rapidly and accurately analyze plan/treatment objectives and patient information to provide RTTP attributes. Using the methods and systems discussed herein, a processor (e.g., the analytics server discussed in FIG. 1) can define treatable sectors based on anatomical site, laterality, and tumor location(s) compared to OARs and body outlines. Moreover, using the treatable sector, the analytics server may limit the search space used by the plan optimizer, such that efficiencies are created. For instance, the plan optimizer may provide an RTTP (e.g., including beam geometry) that complies with various criteria (e.g., best practices) faster, without requiring user intervention, and/or uses less computing resources.

Conventional methods may produce results that violate clinical best practices while not violating the mathematical formula with which they optimize the RTTP. Using the methods and systems discussed herein, a server/computer may use the clinical site, laterality, and tumor location, and other pertinent information to define a treatable sector. The treatable sector can then be ingested by a plan optimizer, such that the plan optimizer can become more efficient. Using the methods and systems discussed herein, the RTTP can be optimized without requiring user intervention, such as user inputs regarding adjusting beam geometries.

Using the methods and systems discussed herein, a machine learning model may be generated with which treatable sectors can be estimated/predicted that are suitable and customized for different patients. For instance, a treatable sector may correspond to patient demographics, patient health-related attributes, tumor attributes, predicted patient movement attributes, and other pertinent patient-specific data. Therefore, using the machine learning model discussed herein, a processor can limit the search space used by a plan optimizer, thereby increasing the plan optimizer's efficiency. For instance, using the machine learning model discussed herein, the plan optimizer can achieve the same/better results than before in less time and/or while using less computing power.

In an embodiment, a method comprises monitoring, by a processor, a treatment plan optimizer computer model to identify a set of treatment plans each comprising treatment planning images, a structure set with planning target volume and organ at risk, and a range of angles for treatment beam entry, where the treatment plan optimizer computer model ingests a set of medical images and predicts each treatment plan comprising a respective range of angles for treatment beam entry; generating, by the processor, a training dataset comprising the monitored data; and training, by the processor, a machine learning model using the training dataset to predict a new range of angles for treatment beam entry for a new patient by ingesting new patient data of the new patient.

The method may comprise transmitting, by the processor, the new range of angles for treatment beam entry to the treatment plan optimizer computer model, whereby the treatment plan optimizer computer model predicts a new treatment plan for the new patient, wherein the treatment plan optimizer uses at least one of static, intensity modulated, volumetric modulated or hybrid field techniques for analyzing the new range of angles, wherein the treatment plan optimizer calculates a final beam geometry that is within the new range of angles.

The new range of angles for treatment beam entry may be calculated based on tumor location or anatomical site of the treatment.

The new range of angles for treatment beam entry may be calculated based on data associated with an organ at risk.

The new range of angles for treatment beam entry may be calculated based on a type or anatomical site of cancer being treated.

The machine learning model may be further configured to predict an avoidance area for the new patient.

The medical images within the training dataset may be converted from a three-dimensional representation to a two-dimensional representation.

The two dimensional representation of medical image may correspond to a beam's eye view.

In another embodiment, a system comprises a computer readable medium storing a set on instructions, that when executed, cause a processor to monitor a treatment plan optimizer computer model to identify a set of treatment plans each comprising treatment planning images, structure set with planning target volume and organ at risk, and a range of angles for treatment beam entry, where the treatment plan optimizer computer model ingests a set of medical images and predicts each treatment plan comprising a respective range of angles for treatment beam entry; generate a training dataset comprising the monitored data; and train a machine learning model using the training dataset to predict a new range of angles for treatment beam entry for a new patient by ingesting new patient data of the new patient.

The set of instructions may further cause the processor to transmit the new range of angles for treatment beam entry to the treatment plan optimizer computer model, whereby the treatment plan optimizer computer model predicts a new treatment plan for the new patient, wherein the treatment plan optimizer uses at least one of static, intensity modulated, volumetric modulated or hybrid field techniques for analyzing the new range of angles, wherein the treatment plan optimizer calculates a final beam geometry that is within the new range of angles.

The new range of angles for treatment beam entry may be calculated based on tumor location or anatomical site of the treatment.

The new range of angles for treatment beam entry may be calculated based on data associated with an organ at risk.

The new range of angles for treatment beam entry may be calculated based on a type or anatomical site of cancer being treated.

The machine learning model may be further configured to predict an avoidance area for the new patient.

The medical images within the training dataset may be converted from a three-dimensional representation to a two-dimensional representation.

The two dimensional representation of medical image corresponds to a beam's eye view.

In another embodiment, a method comprises generating, by a processor, a training dataset comprising a set of previously implemented treatment plans each comprising treatment planning images, structure set with planning target volume and organ at risk, and a range of angles for treatment beam entry, wherein the set of previously implemented treatment plans was generated using a treatment plan optimizer computer model; and training, by the processor, a machine learning model using the training dataset to predict a new range of angles for treatment beam entry for a new patient by ingesting new patient data of the new patient.

The new range of angles for treatment beam entry may be calculated based on data associated with an organ at risk.

The new range of angles for treatment beam entry may be calculated based on a type or anatomical site of cancer being treated.

The machine learning model may be further configured to predict an avoidance area for the new patient.

BRIEF DESCRIPTION OF THE DRAWINGS

Non-limiting embodiments of the present disclosure are described by way of example with reference to the accompanying figures, which are schematic and are not intended to be drawn to scale. Unless indicated as representing the background art, the figures represent aspects of the disclosure.

FIG. 2A illustrates a process flow diagram executed in a plan generation system, according to an embodiment.

FIG. 2B illustrates a process flow diagram executed in a plan generation system, according to an embodiment.

FIG. 4 illustrates a visual representation of treatable sectors, according to an embodiment.

FIGS. 6-16 illustrate various visual representations of non-limiting examples identifying, analyzing, and/or outputting treatable sectors using the plan generation system, accordingly to different embodiments.

DETAILED DESCRIPTION

Figure 1:
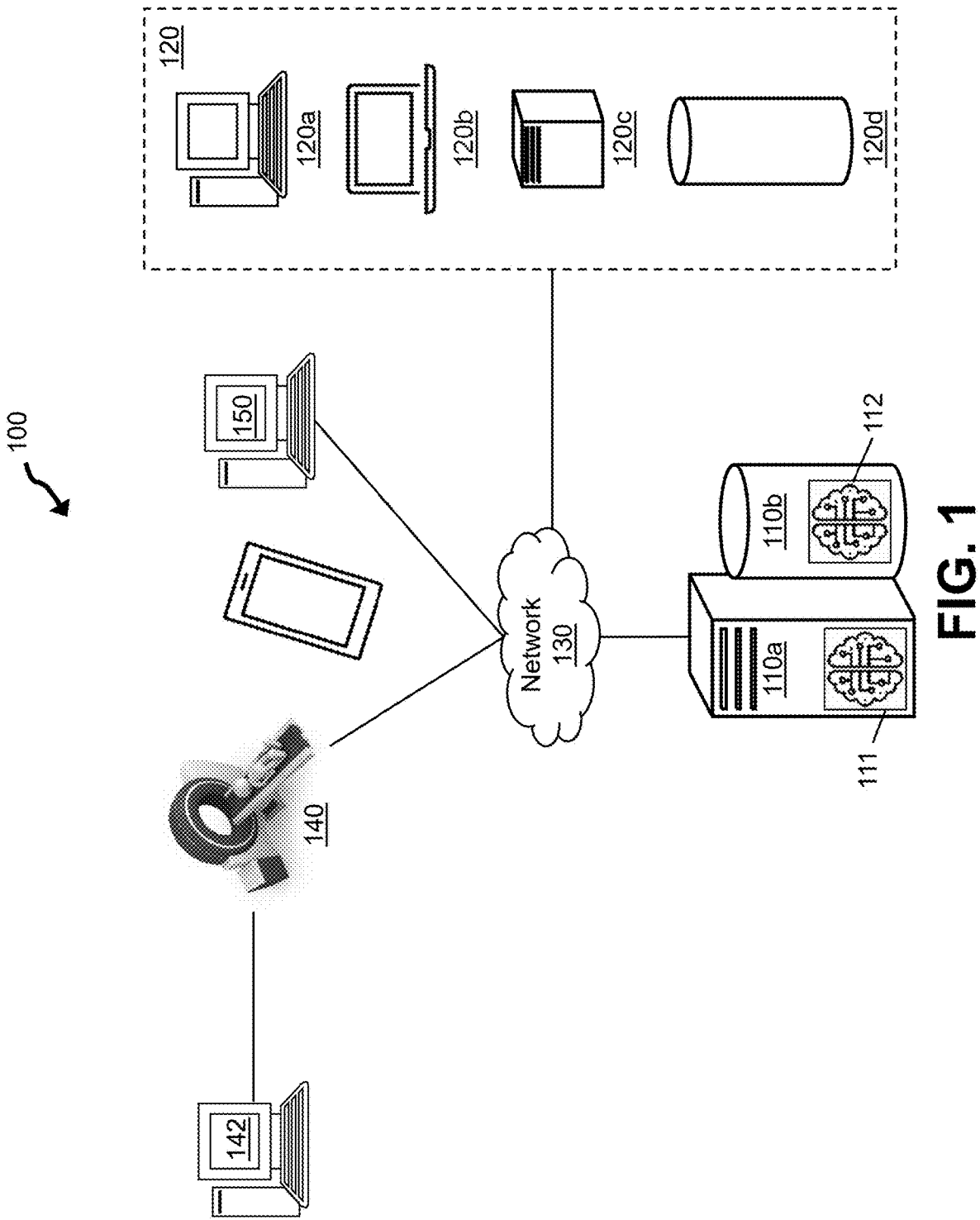
FIG. 1 illustrates components of a plan generation system, according to an embodiment.

Reference will now be made to the illustrative embodiments depicted in the drawings, and specific language will be used here to describe the same. It will nevertheless be understood that no limitation of the scope of the claims or this disclosure is thereby intended. Alterations and further modifications of the inventive features illustrated herein, and additional applications of the principles of the subject matter illustrated herein, which would occur to one skilled in the relevant art and having possession of this disclosure, are to be considered within the scope of the subject matter disclosed herein. Other embodiments may be used and/or other changes may be made without departing from the spirit or scope of the present disclosure. The illustrative embodiments described in the detailed description are not meant to be limiting of the subject matter presented.

FIG. 1 illustrates components of a plan generation system 100 (system 100), according to an embodiment. The system 100 may include an analytics server 110a, system database 110b, treatable sector model 111, end-user devices 120a-d (collectively end-user devices 120), and an administrator computing device 150. Various components depicted in FIG. 1 may belong to a radiation therapy clinic at which patients may receive radiation therapy treatment, in some cases via one or more radiation therapy machines located within the clinic (e.g., medical device 140). The above-mentioned components may be connected through a network 130. Examples of the network 130 may include but are not limited to, private or public LAN, WLAN, MAN, WAN, and the Internet. The network 130 may include wired and/or wireless communications according to one or more standards and/or via one or more transport mediums.

The communication over the network 130 may be performed in accordance with various communication protocols such as Transmission Control Protocol and Internet Protocol (TCP/IP), User Datagram Protocol (UDP), and IEEE communication protocols. In one example, the network 130 may include wireless communications according to Bluetooth specification sets or another standard or proprietary wireless communication protocol. In another example, the network 130 may also include communications over a cellular network, including, e.g., a GSM (Global System for Mobile Communications), CDMA (Code Division Multiple Access), and EDGE (Enhanced Data for Global Evolution) network.

The system 100 is not confined to the components described herein and may include additional or other components, not shown for brevity, which is to be considered within the scope of the embodiments described herein.

The analytics server 110a may generate and display an electronic platform configured to use various computer models 111-112 to identify attributes of an RTTP for a patient's treatment. The electronic platform may include a graphical user interface (GUI) displayed on the end-user devices 120 and/or the administrator computing device 150. An example of the electronic platform generated and hosted by the analytics server 110a may be a web-based application or a website configured to be displayed on different electronic devices, such as mobile devices, tablets, personal computers, and the like.

In a non-limiting example, a physician operating the physician device 120b may access the platform, input patient attributes or characteristics and other data, and further instruct the analytics server 110a to generate an RTTP (including the beam angle). Additionally or alternatively, the analytics server 110a may only optimize a particular attribute of the RTTP (e.g., optimize beam angle only).

The analytics server 110a may recommend the RTTP (e.g., beam angles and other radiation parameters and/or treatment plan attributes) used for proton radiation, photon radiation, and electron radiation. In particular, analytics server 110a may utilize the methods and systems described herein to execute the treatable sector model 111 to identify treatable sectors. Then, the analytics server 110a may use the generated treatable sectors to limit the search space used by the plan optimizer model 112. Further, the analytics server 110a may transmit the beam angles and other radiation parameters and/or treatment plan attributes to one or more other servers. Additionally, or alternatively, the analytics server 110a (another server) may adjust the configuration of one or more devices (e.g., the medical device 140) based on the optimized beam angle. For instance, the RTTP may be directly sent to the medical device 140 and/or the computer 142 that functionally controls the medical device 140.

The medical device 140 may be any medical device used in the radiation therapy treatment of a patient (such as a CT scan machine, radiation therapy machine (e.g., a linear accelerator, particle accelerator (including circular accelerators), or a cobalt machine)). The medical device 140 may also include an imaging device capable of emitting radiation such that the medical device 140 may perform imaging according to various methods to accurately image the internal structure of a patient. For instance, the medical device 140 may include a rotating system (e.g., a static or rotating multi-view system). A non-limiting example of a multi-view system may include stereo systems (e.g., two systems may be arranged orthogonally).

The analytics server 110a may host a website accessible to users operating any of the electronic devices described herein (e.g., end users or medical professionals), where the content presented via the various webpages may be controlled based upon each particular user's role or viewing permissions. The analytics server 110a may be any computing device comprising a processor and non-transitory machine-readable storage capable of executing the various tasks and processes described herein. The analytics server 110a may employ various processors such as central processing units (CPU) and graphics processing unit (GPU), among others. Non-limiting examples of such computing devices may include workstation computers, laptop computers, server computers, and the like. While the system 100 includes a single analytics server 110a, the analytics server 110a may include any number of computing devices operating in a distributed computing environment, such as a cloud environment.

The analytics server 110a may execute software applications configured to display the electronic platform (e.g., host a website), which may generate and serve various webpages to each end-user devices 120. Different users may use the website to view and/or interact with the recommended (optimized) results. Different servers, such as a clinic server 120c may also use the recommended results in downstream processing.

The analytics server 110a may be configured to require user authentication based upon a set of user authorization credentials (e.g., username, password, biometrics, cryptographic certificate, and the like). The analytics server 110a may access the system database 110b configured to store user credentials, which the analytics server 110a may be configured to reference in order to determine whether a set of entered credentials (purportedly authenticating the user) match an appropriate set of credentials that identify and authenticate the user.

The analytics server 110a may generate and host webpages based upon a particular user's role within the system 100. In such implementations, the user's role may be defined by data fields and input fields in user records stored in the system database 110b. The analytics server 110a may authenticate the user and may identify the user's role by executing an access directory protocol (e.g., LDAP). The analytics server 110a may generate webpage content that is customized according to the user's role defined by the user record in the system database 110b.

The analytics server 110a may receive various clinical objectives, patient data, and treatment data from the end-user devices 120. For instance, a physician may access the platform provided by the analytics server 110a using a physician device 120b. The physician may input various patient attributes and/or clinical objectives using one or more input elements of the platform. The analytics server 110a may then execute various methods discussed herein and display an RTTP on the platform.

The end-user devices 120 may be any computing device comprising a processor and a non-transitory machine-readable storage medium capable of performing the various tasks and processes described herein. Non-limiting examples of end-user devices 120 may be a workstation computer, laptop computer, tablet computer, and server computer. In operation, various users may use end-user devices 120 to access the GUI operationally managed by the analytics server 110a. Specifically, the end-user devices 120 may include clinic computer 120a, physician device 120b, clinic server 120c, and clinic database 120d.

In order to generate the RTTP, the analytics server 110a may then execute various models (e.g., treatable sector model 111 and/or a plan optimizer model 112) to analyze the retrieved/received data.

The administrator computing device 150 may represent a computing device operated by a system administrator. The administrator computing device 150 may be configured to display beam angles, radiation parameters, and/or other radiation therapy treatment attributes generated by the analytics server 110a; monitor the treatable sector model 111 utilized by the analytics server 110a, and/or end-user devices 120; review feedback; and/or facilitate training or retraining (calibration) of the models 111-112 that are maintained by the analytics server 110a.

The analytics server 110a may be in communication (real-time or near real-time) with the medical device 140 (or its computer 142), such that a server/computer hosting the medical device 140 can adjust the medical device 140 based on the RTTP (e.g., beam angles, treatment attributes and/or radiation parameters determined by the analytics server 110a). For instance, the radiation therapy machine may adjust the gantry, beam blocking device (e.g. multi-leaf collimator MLC), and couch based on optimized beam angles, where the optimized beam angle is an angle of the medical device 140 that emits radiation in a direction of the PTVs. The analytics server 110a may transmit instructions to the radiation therapy machines indicating any number or type of radiation parameters and/or treatment attributes to facilitate such adjustments.

The models 111 and/or 112 may represent any collection of algorithmic logic and/or artificial intelligence models (e.g., using various machine learning techniques). For instance, the treatable sector model 111 may include various algorithms to identify attributes and characteristics of a treatable sector based on patient data and/or treatment attributes. Using the treatable sector model 111, the analytics server 110a may execute the plan optimizer model 112. For instance, the analytics server 110a may execute the models in conjunction with each other and then revise one or more configuration parameters of the plan optimizer 112. Non-limiting examples of a configuration parameter revised by the analytics server 110a may include a search space that is limited/revised using the attributes of the treatable sector. As a result, the efficiencies discussed herein can be achieved without revising the plan optimizer 112 itself. For instance, the treatable sector model 111 can be executed independently and used in conjunction with an existing plan optimizer. Therefore, the plan optimizer (or the system infrastructure) can be retrofitted using the methods and systems discussed herein. This minimal interference with existing infrastructure allows for the improvement of a plan optimizer without the need to revise its source code.

In some embodiments, the analytics server 110a may collect patient data from various sources not shown in FIG. 1. For instance, the analytics server 110a may monitor and collect patient and treatment attributes associated with previously treated radiotherapy patients to be included in a training dataset. Additionally or alternatively, the analytics server 110a may collect/aggregate other patient data (e.g., data associated with how a set of patients or clinical participants received their respective radiotherapy treatment). Using the collected data, the analytics server 110a may generate a training dataset with which the analytics server 110a can train the treatable sector model 111. As a result, the treatable sector model 111 may be used to limit the search space used by the plan optimizer 112.

FIG. 2A illustrates a flow diagram of a process executed in a plan generation system, according to an embodiment. The method 200 includes steps 210-230. However, other embodiments may include additional or alternative execution steps or may omit one or more steps altogether. The method 200 is described as being executed by a server, similar to the analytics server described in FIG. 1. However, one or more steps of method 200 may also be executed by any number of computing devices operating in the distributed computing system described in FIG. 1. For instance, one or more user computing devices may locally perform part or all the steps described in FIG. 2.

At step 210, the analytics server may monitor a treatment plan optimizer computer model to identify a set of treatment plans, where the treatment plan optimizer computer model ingests a set of medical images and predicts each treatment plan comprising a respective range of angles for treatment beam entry. The analytics server may monitor and collect radiation therapy treatment planning data used for a set of patients (e.g., previously treated patients and/or participants in a clinical trial). The data monitored may be retrieved from any data source, such as queried from one or more databases, inputted by a system administrator, and/or by monitoring a plan computer model.

The monitored and collected radiation therapy treatment planning data may refer to radiation-therapy-specific information associated with the patient and may include patient data, clinic-specific data, and clinical objectives (e.g., treatment requirements, such as dose volume histograms, 3D dose volumes, and attributes whether they are mandatory or preferred by a treating physician). The radiation therapy treatment planning data may refer to data associated with a process in which a medical team (e.g., radiation oncologists, radiation therapists, medical physicists, and/or medical dosimetrists) plan the appropriate external beam radiation therapy or internal brachytherapy treatment techniques for one or more patients. In some configurations, the analytics server may receive the data associated with a patient as a result of different medical professionals' directly inputting the radiation therapy treatment planning data (e.g., via a platform generated/hosted by the analytics server). In other configurations, the radiation therapy treatment planning data may be at least partially retrieved from an internal or external data source.

The radiation therapy treatment planning data may include the data associated with the patient (who was previously treated) and the result of the execution of the treatment plan optimizer computer model. That is, the analytics server may collect data ingested by the treatment plan optimizer computer model (e.g., patient data, treatment attributes, and the like) and the results of the execution of the treatment plan optimizer computer model as well. The analytics server may then aggregate the collected/monitored data. In some embodiments, the analytics server may retrieve data outputted or predicted by the beam angle optimizer computer model, such as arc start and stop angles, data associated with the isocenter, and the like. This data is also referred to sometimes as the results of execution of the treatment plan optimizer computer model or the result data. Additionally or alternatively, the analytics server may monitor and collect data associated with the patient (e.g., patient data).

The patient data may include a patient identifier, patient's electronic health data records, medical images (e.g., CT scans, 4D CT Scans, MRIs, and X-ray images), treatment-specific data (e.g., arc information or treatment type), target organ (e.g., specification and location data to identify the tumor to be eradicated). Additional examples may include non-target organs, dosage-related calculations (e.g., radiation dose distribution within an anatomical region of the patient), and machine-specific recommendations (e.g., couch-gantry orientations and/or arc information). In some configurations, the patient data may also include a structure set that includes data indicating various targets (PTVs) and OARs. For instance, a medical image may be segmented (using various protocols, including receiving input from a clinician and/or AI auto-segmentation methods). The structure set, as used herein, may refer to the data generated as a result of the segmentation (e.g., data indicating the location and/or attributes of the tumor).

In some configurations, the patient data may include anatomy data associated with the patient. For instance, the analytics server may receive/retrieve data associated with the patient's anatomy, such as physical data (e.g., height, weight, and/or body mass index) and/or other health-related data (e.g., blood pressure or other data relevant to the patient receiving radiation therapy treatment). The analytics server may also receive/retrieve data associated with current and/or previous medical treatments received by the patient (e.g., data associated with the patient's previous surgeries).

The patient data may include tumor location and a list (and attributes) of OARs near the tumor. For instance, the tumor location may be directly used by the analytics server in the training process because the tumor location may directly impact attributes of the predicted treatable sector. Tumor data (including the location and grade) may be retrieved and/or extracted by the analytics server. For instance, the tumor location may be identified using the medical image of the patient. Additionally or alternatively, the patient data may include OAR attributes. OAR data may be linked to the treatable sector. For instance, certain organs may be avoided altogether, if possible. Additionally or alternatively, anatomical site of the treatment may be used.

The analytics server may analyze the data received/retrieved and generate additional queries accordingly. For instance, the analytics server may receive/retrieve data associated with one or more medical (or other) devices needed for the patient. The analytics server may retrieve data indicating that the patient suffers from a respiratory medical condition. As a result, the analytics server may generate and transmit a query to one or more electronic data sources to identify whether the patient uses/needs a ventilator. This information may then be used to predict an appropriate treatable sector attributes.

In some configurations, the patient data may include each patient's physical attributes (e.g., height, weight, BMI, and the like). This information can be included within the training dataset, such that the trained treatable sector computer model can identify a correlation between the respective data points. For instance, if the patient has a body mass index (BMI) that is higher than a predetermined threshold, and/or if the patient is utilizing a ventilator, the analytics server may limit the treatable sector and/or may not recommend a full gantry arc. This may be due to the possibility of the gantry colliding with the patient and/or the patient's ventilator. As a result, various entry angles may be eliminated from the list of possible angles that can be used for RTTP calculations.

If necessary, the analytics server may also analyze the patient's medical data records to identify the needed patient attributes. For instance, the analytics server may query a database to identify the patient's BMI. However, because many medical records are not digitalized, the analytics server may not receive the patient's BMI value using simple query techniques. As a result, the analytics server may retrieve the patient's electronic health data and may execute one or more analytical protocols (e.g., natural language processing) to identify the patient's body mass index. In another example, if the analytics server does not receive tumor data (e.g., end-points) the analytics server may execute various image recognition protocols and identify the tumor data.

The analytics server may also receive additional data from one or medical professionals. For instance, a treating oncologist may access a platform generated/hosted by the analytics server and may add, remove, or revise data associated with a particular patient, such as patient attributes, treatment attributes, tumor attributes, the primary site of treatment, tumor stage, end-point, whether the primary tumor has been extended, tumor laterality, and the like. Because tumor staging and the end-level attributes are sensitive information that affects patient treatment, this information is typically inputted by the treating oncologist. In another example, the treating oncologist may specifically indicate whether the treatment should be unilateral or bilateral.

Tumor location data may indicate the primary tumor location with respect to the patient's centerline. Therefore, the location may refer to both laterality of the tumor and its anterior/posterior position. This data may be inputted by the treating oncologist or may be analyzed using various image recognition or segmentation methods executed on the patient's medical images (that are received or retrieved by the analytics server). In some embodiments, this information can also be predicted using a machine-learning model if it is not inputted by the treating oncologist (or otherwise received by the analytics server). Another patient attribute may indicate whether and how close the tumor is to other non-diseased organs. For instance, a tumor to be eradicated may be millimeters away from another organ. This information may change field geometry, as other organs must be avoided.

In some embodiments, the analytics server may receive/retrieve, using a clinic identifier, a file comprising clinic-specific logic indicating treatment attributes of a radiation therapy machine in accordance with at least one of radiation therapy treatment planning data or patient anatomy. Each clinic implementing treatment may have its own rules and protocols regarding radiation therapy treatment. The rules may be expressed as a list of logical equations/sentences (e.g., computer-readable logic/code) referring to how the clinic usually treats patients.

Additionally, the monitored data may include prior treatments. For instance, a patient might have had a treatment on their lungs before, which indicates that the radiation may not be emitted through the patient's left lung. In another example, the patient's age may be included within the training dataset.

Additionally, the monitored data may also include clinical goals and attributes.

At step 220, the analytics server may generate a training dataset comprising the monitored data. The analytics server may pre-process the data monitored and collected in the step 210, such that the training data can be efficiently used for training the treatable sector model.

In some embodiments, the analytics server may pre-process the data and generate the training dataset based on the pre-processed data. In some embodiments, the 3D volumetric data (e.g., medical images) may include the PTV, OARs, and/or other organs. In some embodiments, the 3D volumetric data may include treatment planning images, such as CT images or other medical images. Additionally or alternatively, another 3D input may be a structure set contoured on those CT images. The structure set may include PTV and other target structures and/or OARs. Additionally or alternatively, the 3D volumetric data may correspond to the treatment plan.

The pre-processing may include transforming the 3D volumetric data into a 2D image data. For instance, the analytics server may use beams' eye view (BEV) features, where BEV projections are created from OARs and PTVs within the training dataset. BEV may refer to a 2D view of the patient from the gantry direction (e.g., what projected on a 2D plane). As used herein, BEV may refer to data indicating relative orientation of the patient and different features of the radiotherapy machine from the direction of the gantry. The data may then be transposed into 2D data, such that it can emulate how the beam was emitted (e.g., from the point of view of the beam).

At step 230, the analytics server may train a machine learning model using the training dataset to predict a new range of angles for treatment beam entry for a new patient by ingesting new patient data of the new patient. Using the training dataset generated (and sometimes pre-processed), the analytics server may train a treatable sector model, such that the treatable sector model can predict attributes of a treatable sector for a new patient by ingesting the new patient's data (e.g., medical images). As used herein, patient data ingested by a trained treatable sector model may refer to any attribute of the new patient used to generate a treatment plan for the new patient, such as a medical image of the new patient or a structure set indicating various internal organs (PTVs and/or OARs).

The analytics server may use various machine learning techniques, such as supervised, unsupervised, semi-supervised, and/or reinforcement learning methods to train the treatable sector model. In some embodiments, the training dataset may be unlabeled, such that the treatable sector model can learn to uncover attributes of the training dataset (e.g., attributes of the patients being treated, attributes of the treatment including how the treatment was implemented (specifically which angles)).

In some embodiments, the training dataset may be labeled. For instance, the training dataset may include patient attribute and the treatment attributes may be labeled, such that the treatable sector model can use the labeling to train itself. Specifically, using the labeling, the treatable sector model can learn whether a direction (to emit radiation) is acceptable or not. Specifically, the images included within the training dataset that is transformed to an image from the BEV can indicate whether a direction or an arc angle is appropriate or not (e.g., the treatable sector model may analyze the images and see if overlapping OAR structures exists when/if the radiation is emitted from a particular angle).

Transforming the medical images into a 2D allows the treatable sector model to identify overlapping structure from the point of view of the beam (from the isocenter position). This process allows for more efficient training. In some embodiments, e.g., during training or during generation of the training dataset, the analytics server may normalize the images, such that patient geometry differences are minimized. Additionally, the human reviewers (e.g., clinicians) may respond to BEV images more than 3D mapping or grid points. However, the methods and systems discussed herein is not limited to 2D images. For instance, in some embodiments, the treatable sector model can be trained using 3D images. In those embodiments (where the training dataset only includes a 3D map of the organs), the training dataset may include additional data points indicating isocenter data.

When trained, the treatable sector model may be able to ingest patient data and treatment data associated with a patient, such as tumor locations (e.g., medical images), patient geometry data, and treatment attributes and predict appropriate treatment sectors for the patient. The treatable sector model may also be able to identify avoidance sectors indicating a range of angles not to be used for the patient's radiation therapy treatment. For instance, e.g., when the patient is being treated via a VMAT protocol, the treatable sector model can determine a range of angles with which the VMAT treatment should be avoided. The avoidance sector may indicate that OARs may be at harm.

In some embodiments, the analytics server may customize models for different structures, diseases, and/or different tumor locations. For instance, a model may be customized for breast tumors where the model is trained via a training dataset that only includes data associated with breast cancer patients and/or medical images of breast tumors. In another example, the treatable sector model may be trained/customized based on how the tumor has spread (e.g., whether the tumor is advanced). In another example, the treatable sector model may be customized for a specific type or anatomical site of cancer.

In a non-limiting example, after the treatable sector model has been trained, it can ingest a medical image of a new patient (a patient not included within the training dataset) and/or patient data as defined herein to predict a treatable sector and/or an avoidance sector for the new patient.

Additionally or alternatively, when trained, the treatable sector model may analyze each possible beam direction to identify a range of suitable beam directions (angles) for the treatable sector. Accordingly, the treatable sector model may predict the probability of each beam penetrating through a particular region and how effective it would be in the treatment of the patient. This prediction may deliver more contextual information than the binary prediction for the permissible regions and/or angles. Therefore, the trained treatable sector model may determine a confidence score indicating a likelihood that each beam angle would/could be included within the treatable sector. As a result, the user (e.g. clinician) could review the predicted results and determine the best course of action. For instance, the user may choose to include beam angles with (e.g., a 75% confidence score or more) within the treatable sector.

FIG. 2B illustrates a flow diagram of a process executed in a plan generation system, according to an embodiment. The method 202 includes steps 240-260. However, other embodiments may include additional or alternative execution steps or may omit one or more steps altogether. The method 202 is described as being executed by a server, similar to the analytics server described in FIG. 1. However, one or more steps of method 202 may also be executed by any number of computing devices operating in the distributed computing system described in FIG. 1. For instance, one or more user computing devices may locally perform part or all the steps described in FIG. 2B.

At step 240, the analytics server may receive radiation therapy treatment planning data associated with a radiation therapy of a patient. As discussed herein, the analytics server may receive patient data (e.g., patient demographic data, patient geometry, and medical images), treatment attributes (e.g., acceptance criteria, dose volume histograms, and the like).

At step 250, the analytics server may execute the treatable sector model to identify one or more attributes of a treatable sector for the radiotherapy treatment of the patient, the treatable sector model configured to ingest radiation therapy treatment planning data and clinical objectives to generate the one or more attributes of the treatable sector.

Based on the patient data received and the clinical objectives, the analytics server may execute a computer model (e.g., computer model 111 in FIG. 1) to identify one or more attributes of a treatable sector. The treatable sector may be calculated based on anatomical site, laterality, tumor location compared to OAR(s), and/or body outline of the patient. The computer model may include various pre-programmed logical statements that preclude certain attributes from being included within an RTTP. For instance, the computer model may determine beam entry angles that are not appropriate for certain tumors (e.g., based on tumor locations).

Based on the data received/received (e.g., step 240), the analytics server may infer an intent for the RTTP. The intent may be based on the anatomical site and tumor laterality (e.g., left, right, bilateral, and/or no lateral). An intent for RTTP of a lung cancer patient, for example, can include information indicating that the anatomical site is lung and laterality of right. Based on the received/retrieved data, the computer model may apply one or more pre-defined algorithms to define one or more attributes of a clinically suitable treatable sector.

A treatable sector, as used herein, may refer to a range of allowable attributes of the RTTP. For instance, the treatable sector may refer to a range of allowed field (beam) entry angles in the search space (e.g., spanned by the gantry and couch rotations). In some configurations, the collision can be removed as a possibility when calculating the beam entry angles (using the plan optimizer). That is, the treatable sector model may be trained to predict treatable sectors (indicating directions) that would avoid collision (e.g., between one or more features of the radiotherapy machine, such as the gantry and the patient). In some embodiments, after predicting/setting the treatable sector, another beam geometry optimizer may be used to fill this treatable sector with volumetric modulated arc fields or intensity-modulated fields. The data may then be analyzed by a dose optimizer.

The treatable sector model may use one or more pre-programmed logic and algorithms generated based on the training discussed herein and analyze the clinical site, laterality, and tumor locations. For instance, the treatable sector model may train itself based on previously implemented treatments and their corresponding patient data. During training, the treatable sector model may develop an algorithm that is derived based on commonalities or other rules used for the previously-implemented treatments. The algorithms may include several variables where different variables are weighted differently.

In a non-limiting example, the algorithm may be derived, during training, in accordance with previously implemented treatments of lung cancer in conjunction with clinical objectives and/or clinic-specific rules. In some configurations, the data used to derive the algorithm (also referred to herein as the training data) may be received and monitored during previous radiation therapy treatments provided for prior patients. In another example, the training data may be a dataset that includes treatment objectives (e.g., DVH objectives), RTTPs, projected dose distribution, MLC openings, and control weights associated with previously treated patients.

The training data may be processed via any suitable data augmentation approach (e.g., normalization, encoding, or any combination thereof) to produce a new dataset with modified properties to improve the quality of the data. Using this data (and sometimes in conjunction with other clinical objectives or clinic-specific rules), an algorithm (or a series of algorithms) can be generated that identifies attributes for a treating sector. The algorithm may not exactly identify attributes of the RTTP itself. However, the algorithm may identify attributes of the RTTP that would not be appropriate and should not be included in the RTTP (and as a result should not be considered or evaluated by the plan optimizer). For instance, the algorithm (while not identifying an exact beam angle for the RTTP) can identify what beam angles should not be explored. This may be due to a variety of rules, clinical objectives, and/or clinic-specific requirements.

At step 260, the analytics server may execute a plan optimizer computer model to identify a radiation therapy treatment plan using the received radiation therapy treatment planning data associated with a patient and one or more attributes of the treatable sector.

The plan optimizer computer model may use various data, such as patient data, data received in step 240, and the like to identify RTTP attributes for the patient's radiation therapy treatment. Conventionally, the plan optimizer computer model may use the received data to iteratively calculate an RTTP within a search space. As used herein, a search space may refer to a mathematical space or range for all feasible solutions (the set of solutions among which the desired solution resides). Each point in the search space may represent one variation of a possible attribute used in the RTTP. The plan optimizer computer model may iteratively identify the RTTP attributes using the search space (e.g., using different possibilities of variations for different attributes and permutations). For instance, the plan optimizer computer model may iteratively calculate an RTTP for different values within the search space. After each iteration, the plan optimizer computer model may evaluate the RTTP. The plan optimizer computer model may then repeat the iteration (using a different value from the search space) and compare the RTTPs. The plan optimizer computer model may repeat this process until the RTTP is optimized.

Figure 3:
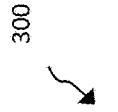
FIG. 3 illustrates different visual representations of treatable sectors, according to an embodiment.

Referring now to FIGS. 3-4, visual illustrations of different treatable sectors are illustrated. For instance, the example 300 illustrates three different patients' anatomies (anatomies 310, 320, and 330). Each anatomy depicts a tumor (PTV 314, 324, and 334) included within each respective patient's lungs (e.g., right lungs 316a, 326a, and 336a and left lungs 316b, 326b, and 336b). Based on the locations of the PTVs (laterality, clinical site, and tumor location), the analytics server may execute the first computer model (e.g., treatable sector computer model) to identify the treatable sectors 312, 322, and 332. In this example, the computer model may first assume head first supine (HFS) treatment orientation and coplanar treatment. The angle for each treatable sector may be defined as the angle between the gantry and the beam defined via a coordination system (e.g., the IEC 61217 FIXED Z-axis that is pointing upward). The algorithm may be defined as a function of tumor laterality and posteriority.

Using the training data set, the analytics server may utilize the treatable sector model to predict three different treatable sectors for the three tumors (PTVs 314, 324, and 334). These three treatable sectors (312, 322, and 332) are examples of treatable sectors for left laterality tumors. The analytics server may calculate the treatable sector 312 as $\phi=[0°, 230°]$ because the PTV 314 is a posterior tumor of the lung 316b. The analytics server may calculate the treatable sector 322 as $\phi=[330°, 220°]$ because the PTV 324 is located more medially in the posterior-anterior direction of the lung 326b. Similarly, the analytics server may calculate the treatable sector 332 as $\phi=[310°, 180°]$ because the PTV 334 is an anterior tumor of the lung 336b.

The treatable sectors depicted in FIG. 3 visually identify a range of beam angles that are appropriate for the patient's RTTP. Therefore, the angles outside the depicted range can be eliminated from the search space used for iterative RTTP optimization calculations. While conventional methods would analyze all the applicable angles to identify the RTTP (including the beam angles), certain beam angles may not yield medically suitable results while satisfying most (if not all) mathematical requirements. For instance, to treat the PTV 314, an RTTP may mathematically identify that the beam should enter from 100°. However, this beam angle will inevitably lead to the beam entering the patient's body from their right lung which could lead to an acceptable plan dose, but an unacceptable beam geometry due to clinical best practices of avoiding beams through the healthy lung. There-fore, mathematical formulas (without the benefit of using the medical context regarding treatable sectors) may lead to results that are mathematically acceptable but not medically acceptable. Limiting the search space used by the algorithm via the treatable sectors identified using the methods and systems discussed herein can result in fewer iterations (e.g., the model may only focus on the treatable sector angle ranges instead of 360°), which can ultimately reduce the computational time and resources needed to optimize a patient's RTTP.

In some embodiments, the analytics server may identify two treatable sectors for a single PTV. Referring now to example 400 depicted in FIG. 4, the analytics server ana-lyzes tumor location for a PTV 402. The example 400 illustrates two treatable sectors 406 and 408 for a patient's esophagus. In the example, the PTV is located between the patient's lungs 410a-b. Because of the PTV's location the analytics server executes the model and identifies two ranges (front and back of the patient) illustrated as the treatable sectors 406 and 408:

$$\phi=[310°,50°] \text{ and } \phi=[140°,220°]$$

Figure 5:
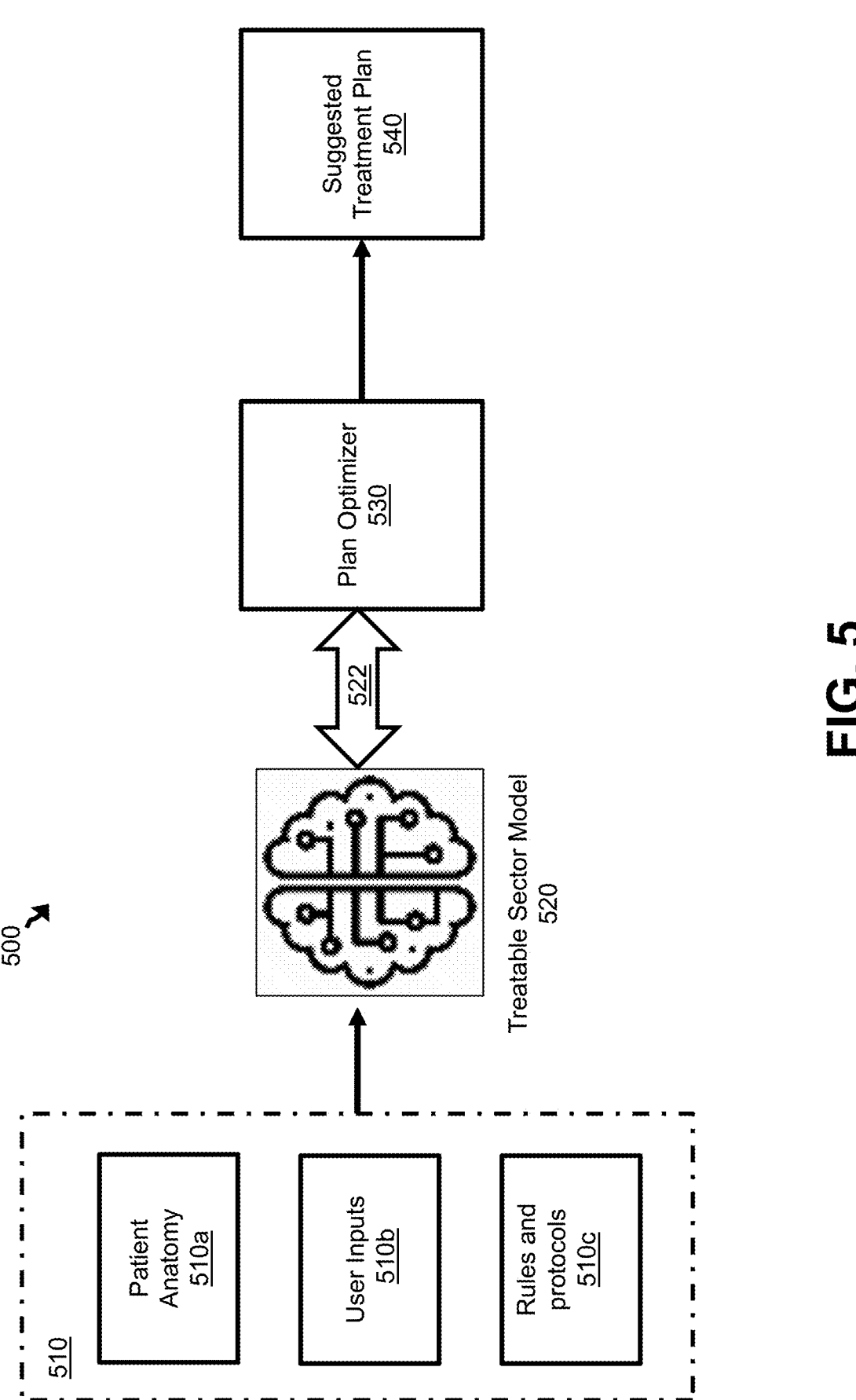
FIG. 5 illustrates a visual representation of a non-limiting example of implementing the plan generation system, according to an embodiment.

Referring now to FIG. 5, a non-limiting visual example of a workflow utilizing the methods and systems described herein is illustrated. In this non-limiting example 500, the analytics server provides treatable sector data to a plan optimizer 530 to generate a suggested RTTP that is opti-mized for a patient and their treatment. The analytics server may first collect patient data 510. The patient data may include patient anatomy data 510a (e.g., medical images, PTVs, OARs), user inputs 510b (clinical objectives or rules received via a user interface from a treating oncologist, such as tumor data, PTV identification, and the like). Other non-limiting examples of clinical goals may include dosi-metric goodness function, robustness metrics, biological effects of radiation, metrics based on linear energy transfer, and the like. The patient data 510 may also include rules 510c for the patient's treatment (e.g., clinical/treatment objectives or criteria identified by the medical professionals or any other special treatments required by the medical professionals).

In some configurations, the analytics server may access a patient's internal/external file and retrieve/extract the needed patient data 510. The analytics server may then execute a treatable sector model 520 to identify various attributes of a treatment sector for the patient using the patient data 510. The results generated via the treatable sector model 520 may be ingested by the plan optimizer 530. The plan optimizer 530 may be a treatment planning and/or monitoring software solution. The plan optimizer 530 may analyze various factors associated with the patient and the patient's treatment to generate and optimize an RTTP for the patient (e.g., field geometry, treatment modality, and radia-tion parameters needed to treat the patient).

In some configurations, the treatable sector model 520 may first predict the treatable sector based on planning images and structure set, as discussed herein. The treatable sector(s) (predicted by the treatable sector model) may be ingested by a beam geometry optimizer (not shown). The beam geometry optimizer may then place the fields or arcs inside the given sector to further analyze and optimize beam geometry. Alternatively, the treatable sector(s) may be used as a start and stop angles for VMAT arcs. After optimizing beam geometry (e.g., after adding the fields), the example 500 may then use a dose optimization protocol to optimize dose levels.

One of the factors considered by the plan optimizer 530 may be the treatable sector attributes identified by the treatable sector model 520. For instance, using the treatable sector attributes, the plan optimizer 530 may limit its search space. As a non-limiting example, when the treatable sector model 520 identifies a range of angles that are not appro-priate, the plan optimizer 530 may eliminate those angles from its iterative calculation process. As a result, one or more iterations associated with the angles identified by the treatable sector model 520 will not be performed. The plan optimizer 530 may use a static, intensity modulated, volu-metric modulated, and/or or hybrid field technique for analyzing the new range of angles (included within the suggested treatment plan 540). As a result, the plan opti-mizer 530 may calculate a final beam geometry that is within the range of angles predicted by the treatable sector model 520.

While the plan optimizer 530 may consider the treatable sector attributes as a factor, the plan optimizer 530 may also overwrite the results identified by the treatable sector model 520. For instance, the RTTP generated by the plan optimizer 530 may not be dictated by the results identified by the treatable sector model 520. The plan optimizer 530 may utilize various cost function analysis protocols where the overall plan is evaluated in light of the other (sometimes more important) factors. In some cases, other factors may be prioritized over the treatable sectors.

The plan optimizer 530 may iteratively revise the patient's RTTP where the plan optimizer 530 iteratively revises different attributes of the RTTP (e.g., field geometry). In some configurations, the plan optimizer 530 may transmit new treatment plan data back to the treatable sector model 520, whereby the treatable sector model 520 can recalculate/re-predict data based on the revised treatment data generated by the plan optimizer (iteration 522). The plan optimizer 530 and the treatable sector model 520 may repeat the iteration 522 until the patient's RTTP is optimized.

When the plan optimizer completes the patient's RTTP, the plan optimizer 330 may transmit the suggested treatment plan 540 to one or more electronic devices where a user (e.g., clinician) can review the suggested plan. For instance, the suggested treatment plan 540 may be displayed on a computer of a clinic where a radiation therapy technician or a treating oncologist can review the treatment plan.

Referring now to FIG. 6, an example of medical images within a training dataset is depicted, in accordance with an embodiment. The medical image 600 represent one of many medical images (e.g., 40 images) of patients' breasts (20 left images and 20 right images). The training dataset may also include 32 whole breast and to axilla cases (depicted in the medical image 602) (16 left and 16 right) with structures and treatment plans. The training dataset may also include data indicating that the maximum gantry angle used to treat the depicted tumor is 160°-170° for left breast and respectively 200°-190° for right breast.

Figure 7:
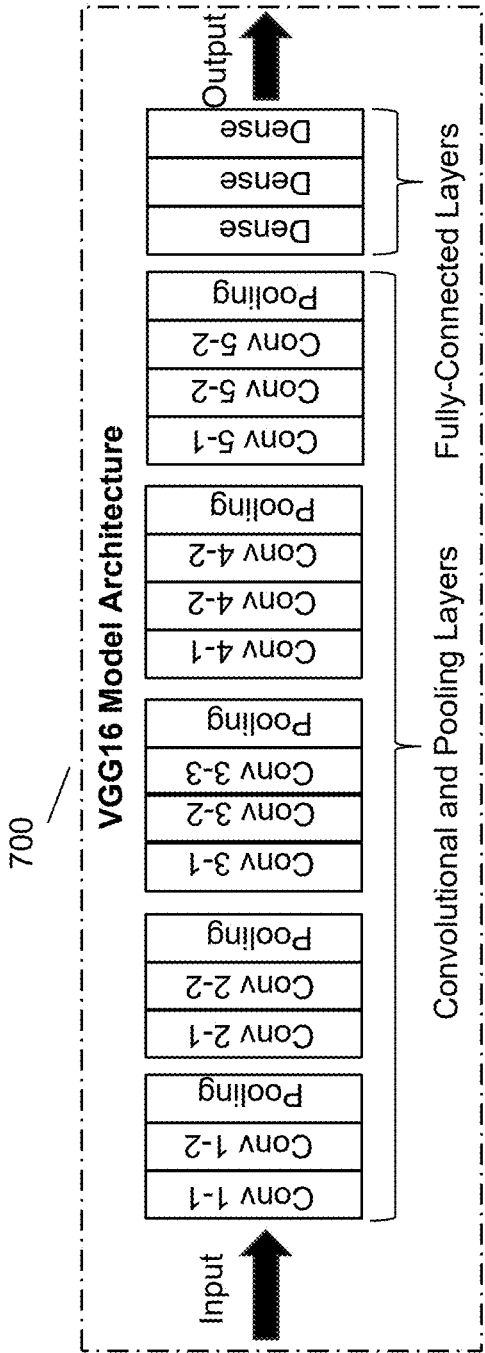

Using the methods and systems discussed herein, the analytics server may train a neural network, such as depicted in FIG. 7. The analytics server may use BEV features, where BEV projections are created from OARs and PTVs, such as the medical images 600 and 602. The non-limiting example of a machine learning model used can be a neural network 700, which is a VGG16 type architecture that has been modified for the BEV case (e.g., delta=3 deg BEV features with "2×CCM+3×CCCM" neural network (e.g., trained with cleaned and pro-processed dataset). The neural network 700 may include various convolutional layers and pooling layers, as depicted.

When trained, the neural network 700 may intake arc start and stop angles, isocenter, BEV images of PTV and other structures (e.g., heart, ipsi lung, spinal cord and contra breast if contoured). The neural network 700 may also ingest treatment attributes inputted by a physician or a clinician, such as various acceptance criteria regarding the patient's treatment and DVHs. For instance, a first acceptance criteria indicating that no field angles should come from:

180° to 280° CW in left breast cases; or

80° to 180° CW in right breast cases.

Another acceptance criteria may indicate that the breast should be covered with arc and the arc should be avoiding majority of entry through contra breast and spinal cord.

As a result, the neural network 700 may predict the results depicted in FIG. 8. Specifically, the neural network 700 may predict the average predicted posterior angles and true averages, as depicted in the chart 800. The results may be validated against a validation dataset, depicted in the chart 810.

Figure 9:
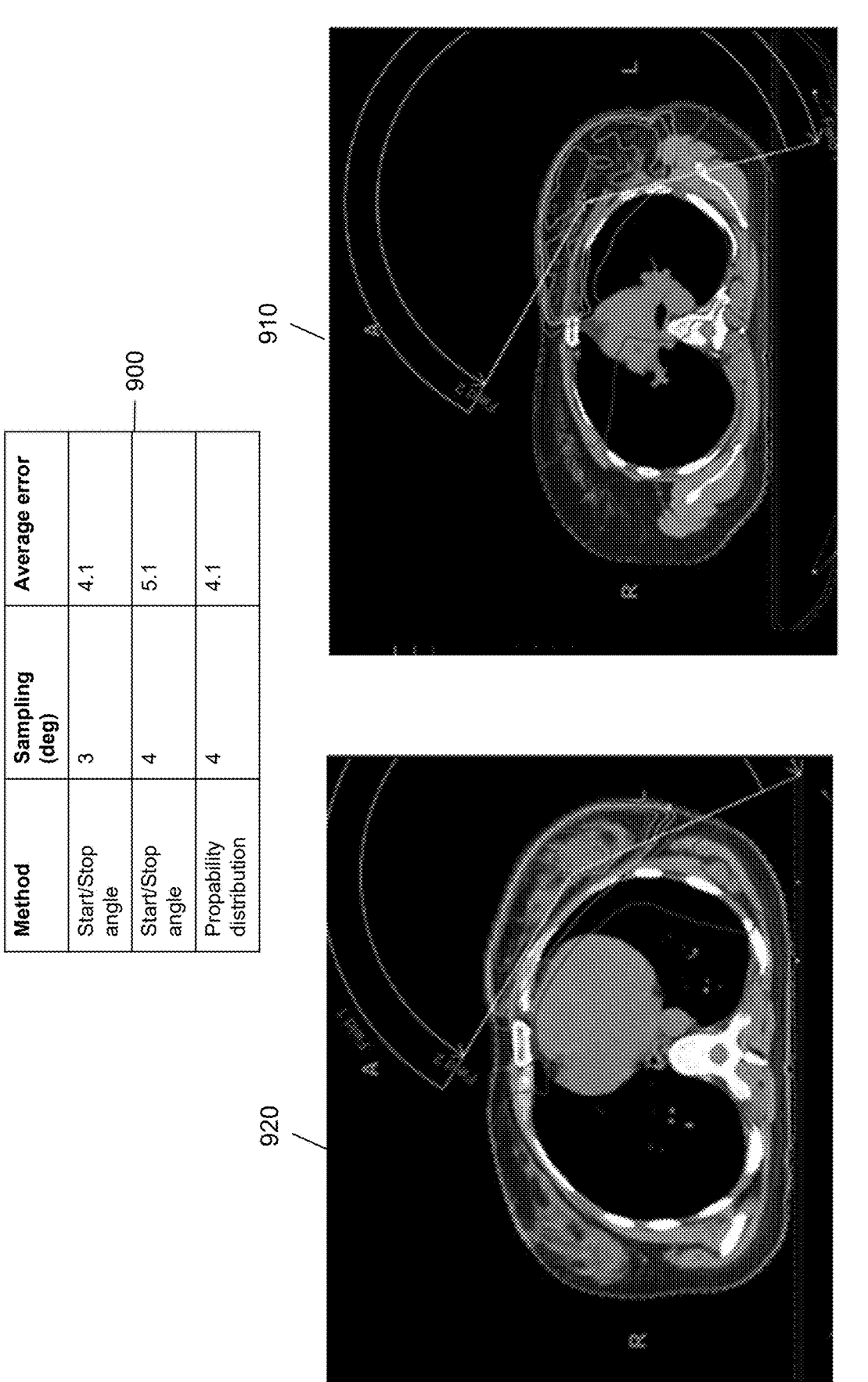

As depicted in FIG. 9, the chart 900 and medical images 910-920 include results predicted by the neural network 700. The chart 900 indicates that the acceptance criteria have been implemented and the results comply with the acceptance criteria. The medical images 910-920 also indicate the predicted start and stop angles (combined with intelligent optimization engine) using 2 arcs and collimator angles 15° and −15° (the medical image 910).

The results predicted by the neural network 700 may be transmitted to other computers, such as the plan optimizer computer model. The plan optimizer may then use the parameters predicted by the treatable sector computer model to generate a treatment plan for the patient.

Figure 10:
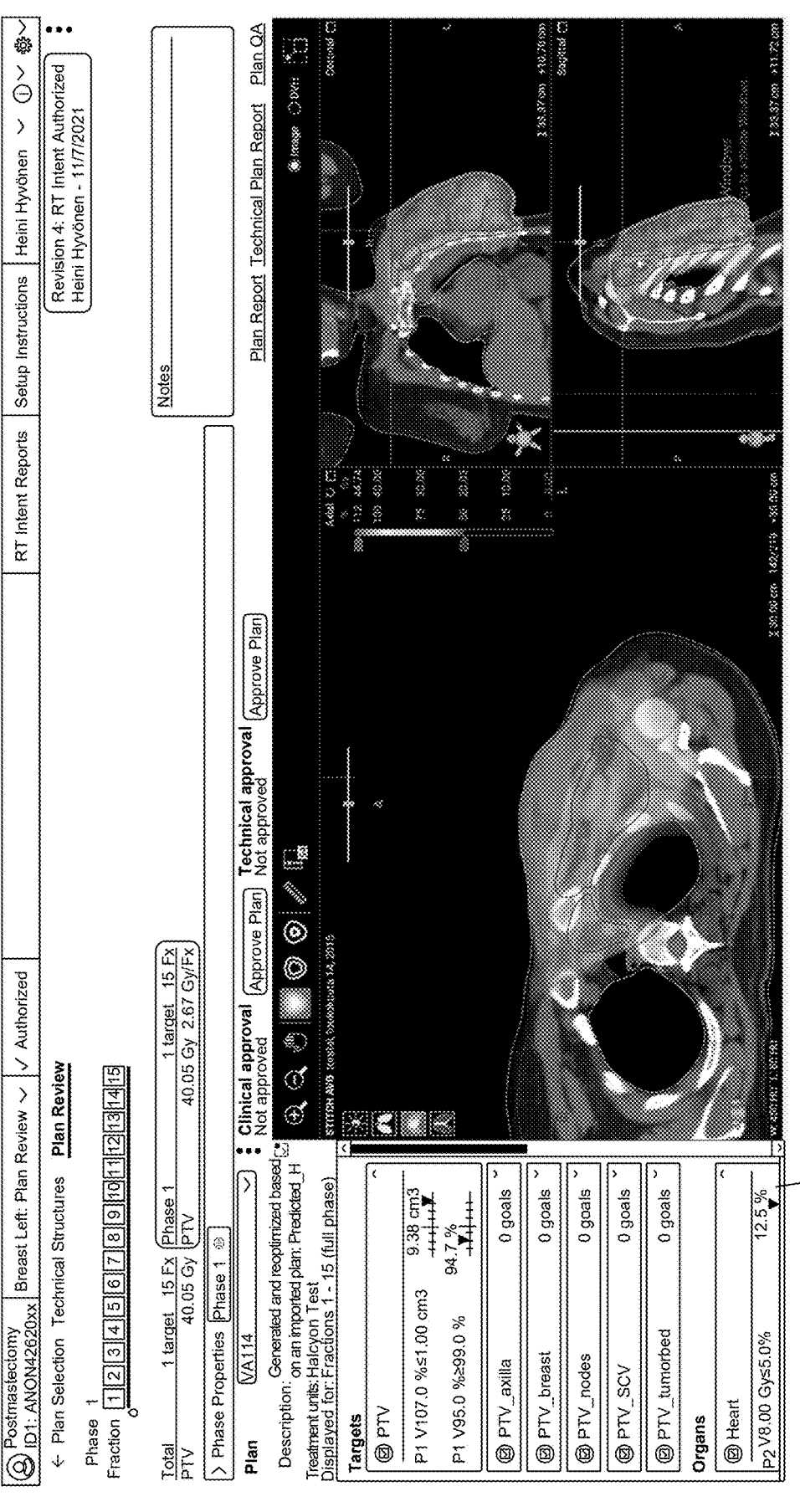
Figure 12:
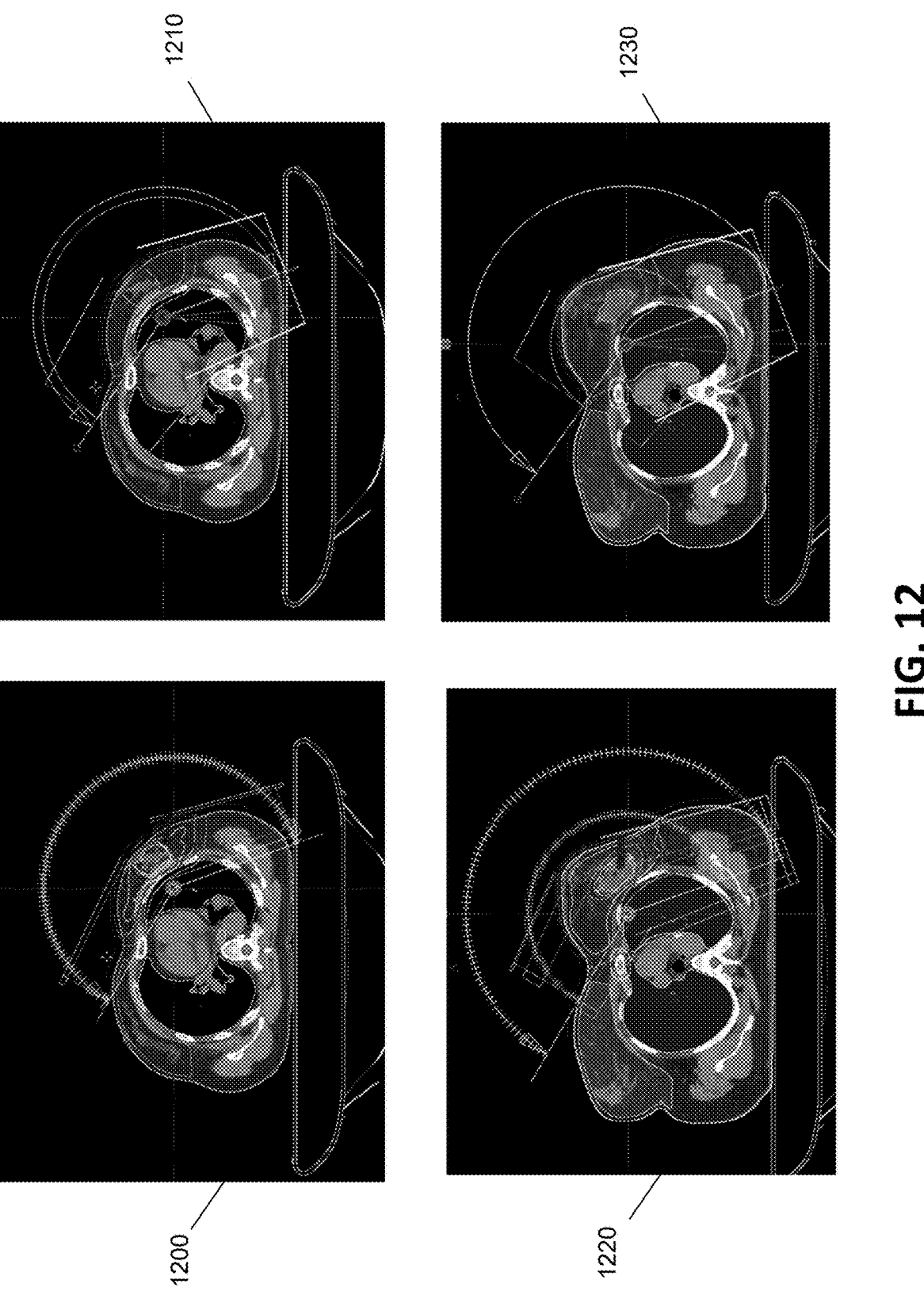
Figure 13:
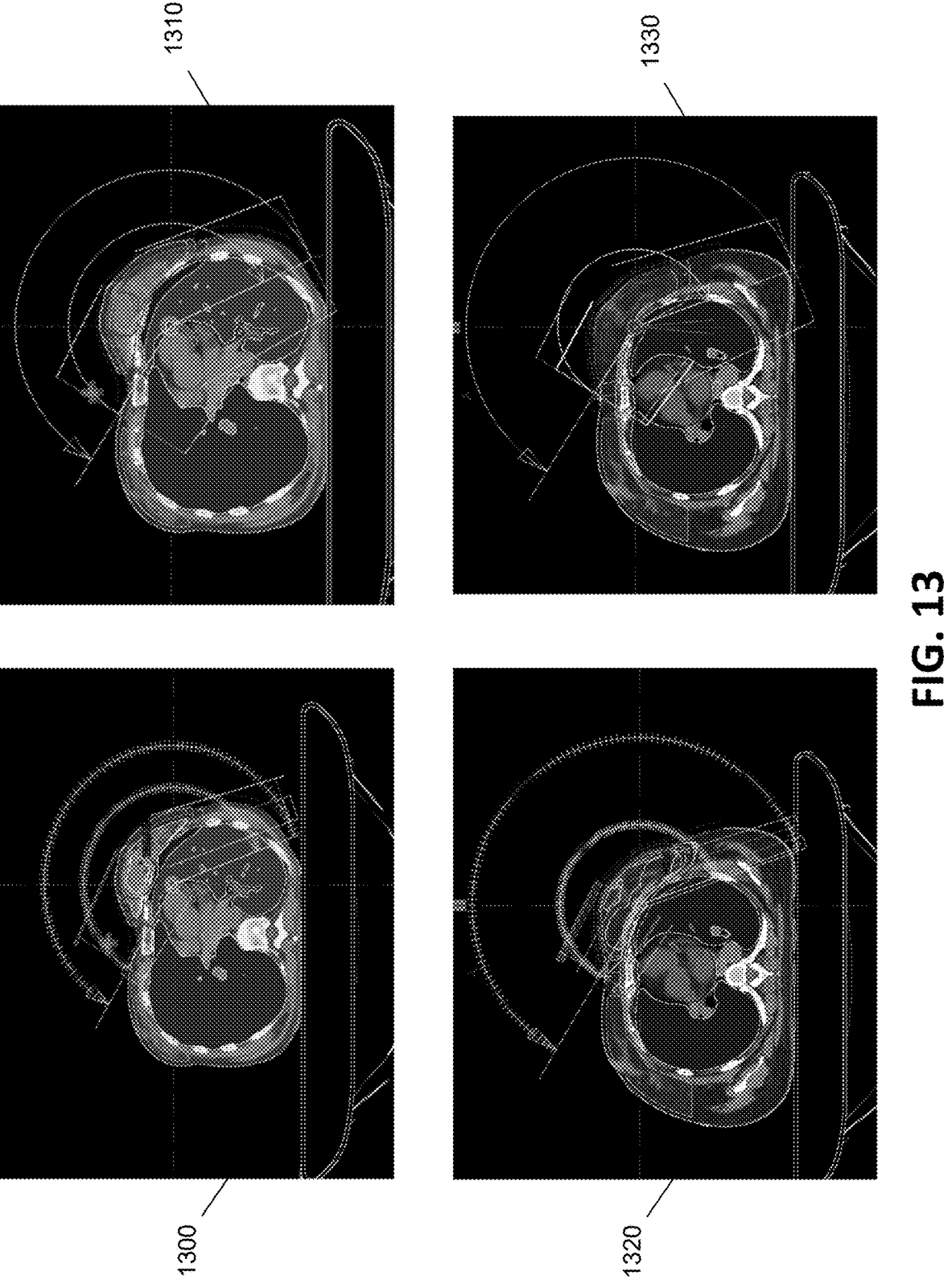
Figure 14:
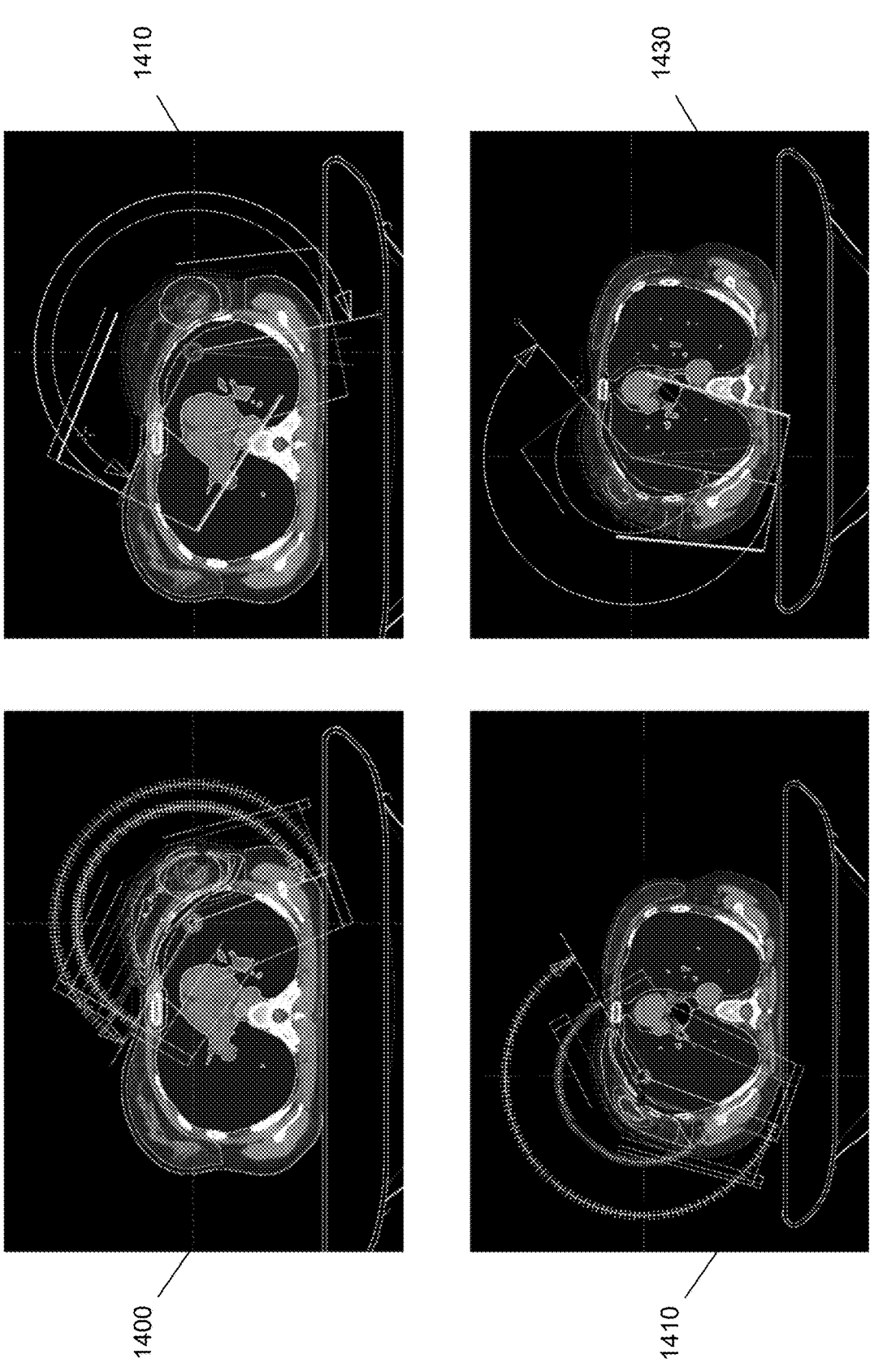

In addition to transmitting the results to other computer models (e.g., plan optimizer), the results predicted by the neural network 700 can be displayed on a graphical user interface, such as the GUI 1000, depicted in FIG. 10. As depicted, the treatable sectors can be combined with intelligent optimization engine (IOE) data. For instance, visual elements may be added to template geometries, trajectory optimizers or other beam geometry optimizers. For instance, as depicted, dosage and/or axial data can be combined an visualized with treatable sectors.

Referring now to FIGS. 11-16, another embodiment of using the machine learning model discussed herein is depicted. FIGS. 11-16 depict results for treatable sector prediction for 7 validation cases that are not included in the training data (e.g., new range of angles for new patients). Specifically, FIG. 11 depicts results predicted by the treatable sector model discussed herein. Specifically, the chart 1100 depicts angle boundaries for the different predicted treatable sectors (each depicted in one row). The treatable sector model may predict/calculate start and stop angles for each case and display the results.

FIGS. 12-15 depict a comparison between VMAT arcs calculated using other methods and VMAT arcs predicted by the treatable sector model. For instance, VMAT arcs depicted in medical images 1200, 1220, 1300, 1320, 1400, and 1420 correspond to VMAT arcs calculated using other methods and VMAT arcs 1210, 1230, 1310, 1330, 1410, and 1430 correspond to VMAT arcs predicted using the methods and systems discussed herein.

The comparison between the VMAT arcs and predicted VMAT arcs indicates that the treatable sector model (trained and executed using the methods and systems discussed herein) achieves substantially (if not exactly) the same results.

In some embodiments, the treatable sector model may distinguish between the two types of breast cases: whole breast (FIG. 15) and whole breast and axilla area (FIG. 16). The first group may refer to early stage breast cancer cases and the second group may refer to more advanced stages of breast cancer cases.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of this disclosure or the claims.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc., may be passed, forwarded, or transmitted via any suitable means including memory sharing, message passing, token passing, network transmission, etc.

The actual software code or specialized control hardware used to implement these systems and methods is not limiting of the claimed features or this disclosure. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the embodiments described herein and variations thereof. Various modifications to these embodiments will be readily apparent to those skilled in the art, and the principles defined herein may be applied to other embodiments without departing from the spirit or scope of the subject matter disclosed herein. Thus, the present disclosure is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What we claim is:

1. A method comprising:

monitoring, by a processor, a treatment plan optimizer computer model to identify a set of treatment plans each comprising treatment planning images, structure set with planning target volume and organ at risk, and a range of angles for treatment beam entry, where the treatment plan optimizer computer model ingests a set of medical images and predicts each treatment plan comprising a respective range of angles for treatment beam entry;

generating, by the processor, a training dataset comprising the monitored data;

training, by the processor, a machine learning model using the training dataset to predict a new range of angles for treatment beam entry for a new patient by ingesting new patient data of the new patient; and causing, by the processor, the treatment plan optimizer to limit a search space associated with a new treatment plan for the new patient in accordance with the new range.

2. The method of claim 1, further comprising:

transmitting, by the processor, the new range of angles for treatment beam entry to the treatment plan optimizer computer model, whereby the treatment plan optimizer computer model predicts a new treatment plan for the new patient, wherein the treatment plan optimizer uses at least one of static, intensity modulated, volumetric modulated or hybrid field techniques for analyzing the new range of angles, wherein the treatment plan optimizer calculates a final beam geometry that is within the new range of angles.

3. The method of claim 1, wherein the new range of angles for treatment beam entry is calculated based on tumor location or anatomical site of the treatment.

4. The method of claim 1, wherein the new range of angles for treatment beam entry is calculated based on data associated with an organ at risk.

5. The method of claim 1, wherein the new range of angles for treatment beam entry is calculated based on a type or anatomical site of cancer being treated.

6. The method of claim 1, wherein the machine learning model is further configured to predict an avoidance area for the new patient.

7. The method of claim 1, wherein the set of medical images within the training dataset are converted from a three-dimensional representation to a two-dimensional representation.

8. The method of claim 1, wherein the two dimensional representation of medical image corresponds to a beam's eye view.

9. A system comprising:

a non-transitory computer readable medium storing a set of instructions, that when executed, cause a processor to:

monitor a treatment plan optimizer computer model to identify a set of treatment plans each comprising treatment planning images, structure set with planning target volume and organ at risk, and a range of angles for treatment beam entry, where the treatment plan optimizer computer model ingests a set of medical images and predicts each treatment plan comprising a respective range of angles for treatment beam entry;

generate a training dataset comprising the monitored data;

train a machine learning model using the training dataset to predict a new range of angles for treatment beam entry for a new patient by ingesting new patient data of the new patient;

cause the treatment plan optimizer to limit a search space associated with a new treatment plan for the new patient in accordance with the new range.

10. The system of claim 9, wherein the set of instructions further cause the processor to:

transmit the new range of angles for treatment beam entry to the treatment plan optimizer computer model, whereby the treatment plan optimizer computer model predicts a new treatment plan for the new patient, wherein the treatment plan optimizer uses at least one of static, intensity modulated, volumetric modulated or hybrid field techniques for analyzing the new range of angles, wherein the treatment plan optimizer calculates a final beam geometry that is within the new range of angles.

11. The system of claim 9, wherein the new range of angles for treatment beam entry is calculated based on tumor location or anatomical site of the treatment.

12. The system of claim 9, wherein the new range of angles for treatment beam entry is calculated based on data associated with an organ at risk.

13. The system of claim 9, wherein the new range of angles for treatment beam entry is calculated based on a type or anatomical site of cancer being treated.

14. The system of claim 9, wherein the machine learning model is further configured to predict an avoidance area for the new patient.

15. The system of claim 9, wherein the set of medical images within the training dataset are converted from a three-dimensional representation to a two-dimensional representation.

16. The system of claim 15, wherein the two dimensional representation of medical image corresponds to a beam's eye view.

17. A method comprising:

generating, by a processor, a training dataset comprising a set of previously implemented treatment plans each comprising treatment planning images, structure set with planning target volume and organ at risk, and a range of angles for treatment beam entry,, wherein the set of previously implemented treatment plans was generated using a treatment plan optimizer computer model;

training, by the processor, a machine learning model using the training dataset to predict a new range of angles for treatment beam entry for a new patient by ingesting new patient data of the new patient; and causing, by the processor, the treatment plan optimizer to limit a search space associated with a new treatment plan for the new patient in accordance with the new range.

18. The method of claim 17, wherein the new range of angles for treatment beam entry is calculated based on data associated with an organ at risk.

19. The method of claim 17, wherein the new range of angles for treatment beam entry is calculated based on a type or anatomical site of cancer being treated.

20. The method of claim 17, wherein the machine learning model is further configured to predict an avoidance area for the new patient.

* * * * *